(12) United States Patent
Hong et al.

(10) Patent No.: US 9,708,242 B2
(45) Date of Patent: Jul. 18, 2017

(54) METHOD OF MANUFACTURING NITRONE COMPOUND

(71) Applicant: National Chung Cheng University, Min-Hsiung Township (TW)

(72) Inventors: Bor-Cherng Hong, Min-Hsiung Township (TW); Cheng-Wei Lin, Changhua (TW)

(73) Assignee: National Chung Cheng University, Min-Hsiung Township (TW)

( * ) Notice: Subject to any disclaimer, the term of this patent is extended or adjusted under 35 U.S.C. 154(b) by 0 days.

(21) Appl. No.: 14/931,385

(22) Filed: Nov. 3, 2015

(65) Prior Publication Data

US 2017/0036989 A1    Feb. 9, 2017

(30) Foreign Application Priority Data

Aug. 6, 2015   (TW) .............................. 104125714 A

(51) Int. Cl.

| | | |
|---|---|---|
| *C07C 291/06* | (2006.01) | |
| *C07D 213/53* | (2006.01) | |
| *C07C 205/03* | (2006.01) | |
| *C07C 205/51* | (2006.01) | |
| *C07D 207/06* | (2006.01) | |
| *C07D 311/80* | (2006.01) | |
| *B01J 31/18* | (2006.01) | |
| *C07C 291/02* | (2006.01) | |
| *C07C 205/45* | (2006.01) | |

(52) U.S. Cl.
CPC ......... *C07C 205/03* (2013.01); *B01J 31/1815* (2013.01); *C07C 205/45* (2013.01); *C07C 205/51* (2013.01); *C07C 291/02* (2013.01); *C07D 207/06* (2013.01); *C07D 213/53* (2013.01); *C07D 311/80* (2013.01); *B01J 2231/44* (2013.01); *B01J 2531/821* (2013.01); *B01J 2531/827* (2013.01)

(58) Field of Classification Search
None
See application file for complete search history.

(56) References Cited

U.S. PATENT DOCUMENTS 6,762,322 B1 *  7/2004  Parker ................. C07D 273/00
                                                      564/253
6,815,459 B2    11/2004  Ko et al.

FOREIGN PATENT DOCUMENTS

WO           9803478 A1    1/1998

OTHER PUBLICATIONS

Wubbels e al, JACS, vol. 96, No. 21, pp. 6698-6706 (1974).*
Cheng-Wei Lin et al, Organic Letters, 2015, 17 (10), pp. 2314-2317, published on the Web: Apr. 20, 2015.*
Cheng-Wei Lin et al, ChemInform, Sep. 2015, vol. 46 (38), Abstract.*
Office Action of corresponding TW application, published on Feb. 23, 2017.

* cited by examiner

*Primary Examiner* — Zinna Northington Davis
(74) *Attorney, Agent, or Firm* — Wang Law Firm, Inc.

(57) ABSTRACT

A method of manufacturing nitrone compounds is provided. The method includes: providing a nitro compound; and performing a photoreaction of the nitro compound, a catalyst and an additive under visible light to obtain the nitrone compound.

6 Claims, 4 Drawing Sheets

METHOD OF MANUFACTURING NITRONE COMPOUND

CROSS-REFERENCE TO RELATED APPLICATION

This application claims priority from Taiwan Patent Application No. 104125714, filed on Aug. 6, 2015, in the Taiwan Intellectual Property Office, the content of which are hereby incorporated by reference in their entirety for all purposes.

BACKGROUND OF THE INVENTION

1. Field of the Invention

The present invention relates to a manufacturing method, in particular with respect to a manufacturing method of manufacturing nitrone compound.

2. Description of the Related Art

Nitrone compound is a key intermediate for the synthesis of naturally occurring compounds or medical drugs. Nitrone compound is well-known for trapping free radicals. Recently, several nitrone compounds have demonstrated potent biological activity against many diseases, such as aging, Alzheimer's disease, cancer, Parkinson disease and stroke.

Nitrone compounds have usually been prepared by condensation reactions between carbonyl compounds and hydroxylamines. Wherein hydroxylamines can be obtained by oxidation of amines or imines or by reduction of nitro compound. However, the strong reactive agents or reaction conditions are necessary. Other recent preparations include copper-mediated coupling of fluorenone oxime and vinyl boronic acid and cyclization of β-allenyloximes.

SUMMARY OF THE INVENTION

In view of the aforementioned technical problems of the prior art, one purpose of the present invention is to provide a method of manufacturing nitrone compound so as to solve the problem of using strong reactive agents or reaction conditions to prepare nitrone compounds in prior art.

In order to accomplish the preceding purpose, the present invention provides a method of manufacturing nitrone compound, comprising: providing a nitro compound; and performing a photoreaction of the nitro compound, a catalyst and an additive under visible light to obtain the nitrone compound.

Wherein the catalyst is $Ru(bpy_3)Cl_2 \cdot 6H_2O$, $Ru(bpy_3)Cl_2$, $Ru(bpy)_3(BF_4)_2$, $Ru(bpy)_3(PF_6)_2$, $Ir[dF(CF_3)ppy]_2(dtbbpy)(PF_6)$ or $Ir(ppy)_2(dtbbpy)(PF_6)$.

Wherein a wavelength of the visible light is within the range of 350 to 700 nm. Preferably, a wavelength of the visible light is within the range of 450 to 460 nm.

Wherein the nitro compound is a second order or third order nitro compound.

Wherein the additive is diisopropylethylamine (DIPEA), diisopropylisobutylamine (DIPIBA) or a derivative of 1,4-Dihydropyridine (DHP). When the additive is diisopropylisobutylamine (DIPIBA), an aldehyde compound is further added in the photoreaction. The derivative of 1,4-Dihydropyridine (DHP) is Hantzsch ester.

Wherein the catalyst is performed a photoredox catalyst reaction in the photoreaction.

In accordance with the preceding description, a method of manufacturing nitrone compound may have one or more following advantages:

(1) In the method of the present invention, the photoreaction is performed under visible light by the nitro compound, the catalyst and the additive, and the nitrone compound can be manufactured under mild condition.

(2) In the method of the present invention, the nitrone compounds can be manufactured by only using available visible light and catalyst without heating or using strong reactive chemicals or materials needed protected.

(3) In the method of the present invention, the nitrone compounds having various substituents can be manufactured by choosing various nitro compounds, additives or aldehydes.

DETAILED DESCRIPTION OF THE PREFERRED EMBODIMENTS

The detailed structure, operating principle and effects of the present invention will now be described in more details hereinafter with reference to the accompanying drawings that show various embodiments of the invention as follows.

Figure 1:
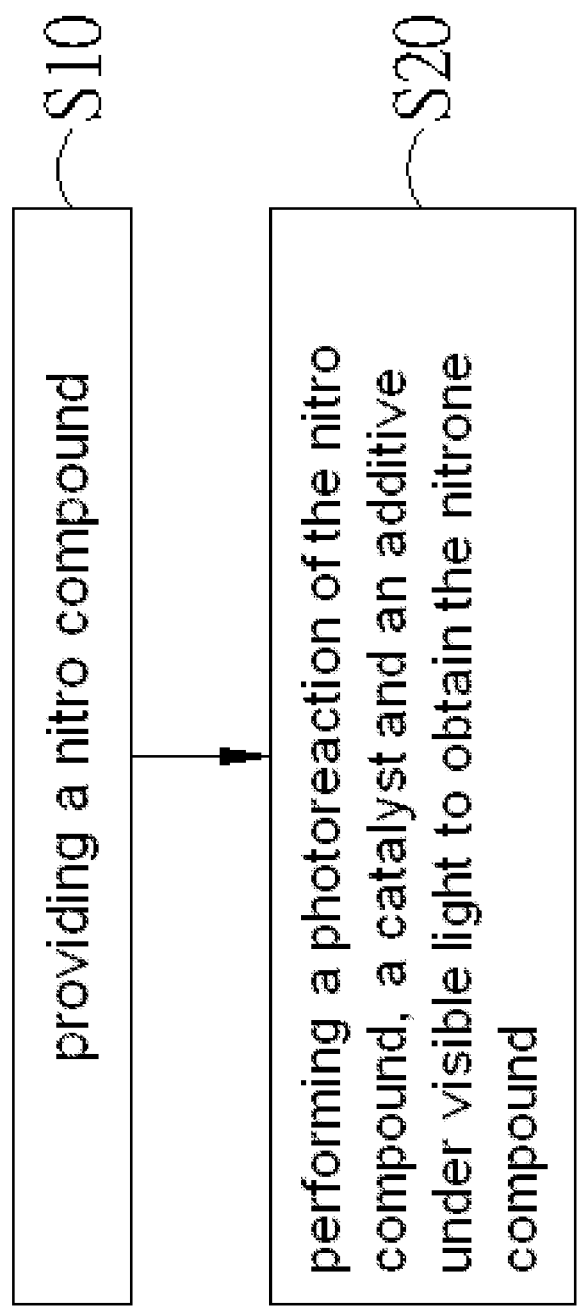
FIG. 1 is a schematic flow diagram showing the method of manufacturing nitrone compound of the present invention.

Refer to FIG. 1, the present invention provides a method of manufacturing nitrone compound, comprising: providing a nitro compound S10; and performing a photoreaction of the nitro compound, a catalyst and an additive under visible light to obtain the nitrone compound S20.

The catalyst is, for example, $Ru(bpy_3)Cl_2 \cdot 6H_2O$, $Ru(bpy_3)Cl_2$, $Ru(bpy)_3(BF_4)_2$ or $Ru(bpy)_3(PF_6)_2$. In the preceding examples, the catalyst which can produce $Ru(bpy_3)$ (II) ion in the reaction can be used as the catalyst used in the present invention. Wherein, the different counter anions of the catalyst will only affect the yield of manufactured nitrone compounds. Further, the catalysts are not limited to the preceding bipyridine (bpy) derivatives, and the derivatives of bipyrazine or bipyrimidine can also be used as the catalyst of the present invention depending upon actual demand. Moreover, the catalyst can also be the catalyst comprising iridium (Ir) metal, such as $Ir[dF(CF_3)ppy]_2(dtbbpy)(PF_6)$ or $Ir(ppy)_2(dtbbpy)(PF_6)$. However, $Ir(ppy)_3$ can not be used to perform the reaction of the present invention.

The wavelength of the visible light can be, for example, within the range of 350 to 700 nm. Preferably, the wavelength of the visible light can be, for example, within the range of 450 to 460 nm. Wherein, the nitro compound can be a second order or third order nitro compound. The additive can be diisopropylethylamine (DIPEA) (formula I), diisopropylisobutylamine (DIPIBA) (formula II) or derivatives of 1,4-Dihydropyridine (DHP) (formulas III and IV). Wherein, when the additive is diisopropylisobutylamine (DIPIBA), the aldehyde compound is further added in the photoreaction. Wherein, the catalyst can perform the photoredox catalyst reaction in the photoreaction. The derivative of 1,4-Dihydropyridine (DHP) can be, for example, Hantzsch ester (formula III). The kinds of preceding catalysts and additives and the wavelength of the visible light are not limited thereto.

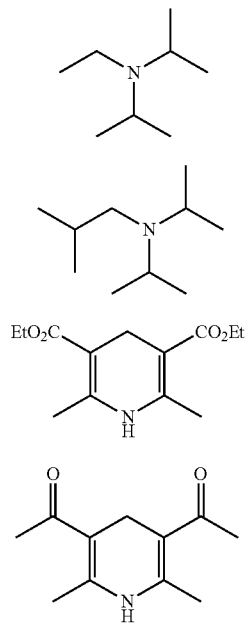

Further, the additives can also be the derivatives of formula I, II, III or IV. For example, the additives can be:

| R¹ | R² | R³ |
|---|---|---|
| H$^{bi}$ | CH$_3$ | OCH$_3$ |
| CH$_3$CH$_2$CH$_2$ | CH$_3$ | OCH$_3$ |
| 3-NO$_2$—C$_6$H$_4$ | CH$_3$ | OCH$_3$ |
| H | CH$_3$ | CH$_3$ |
| CH$_3$CH$_2$CH$_2$ | CH$_3$ | CH$_3$ |
| 3-NO$_2$—C$_6$H$_4$ | CH$_3$ | CH$_3$ |
| H | | —CH$_2$CH$_2$CH$_2$— |
| CH$_3$CH$_2$CH$_2$ | | —CH$_2$CH$_2$CH$_2$— |
| 3-NO$_2$—C$_6$H$_4$ | | —CH$_2$CH$_2$CH$_2$— |

Figure 2:
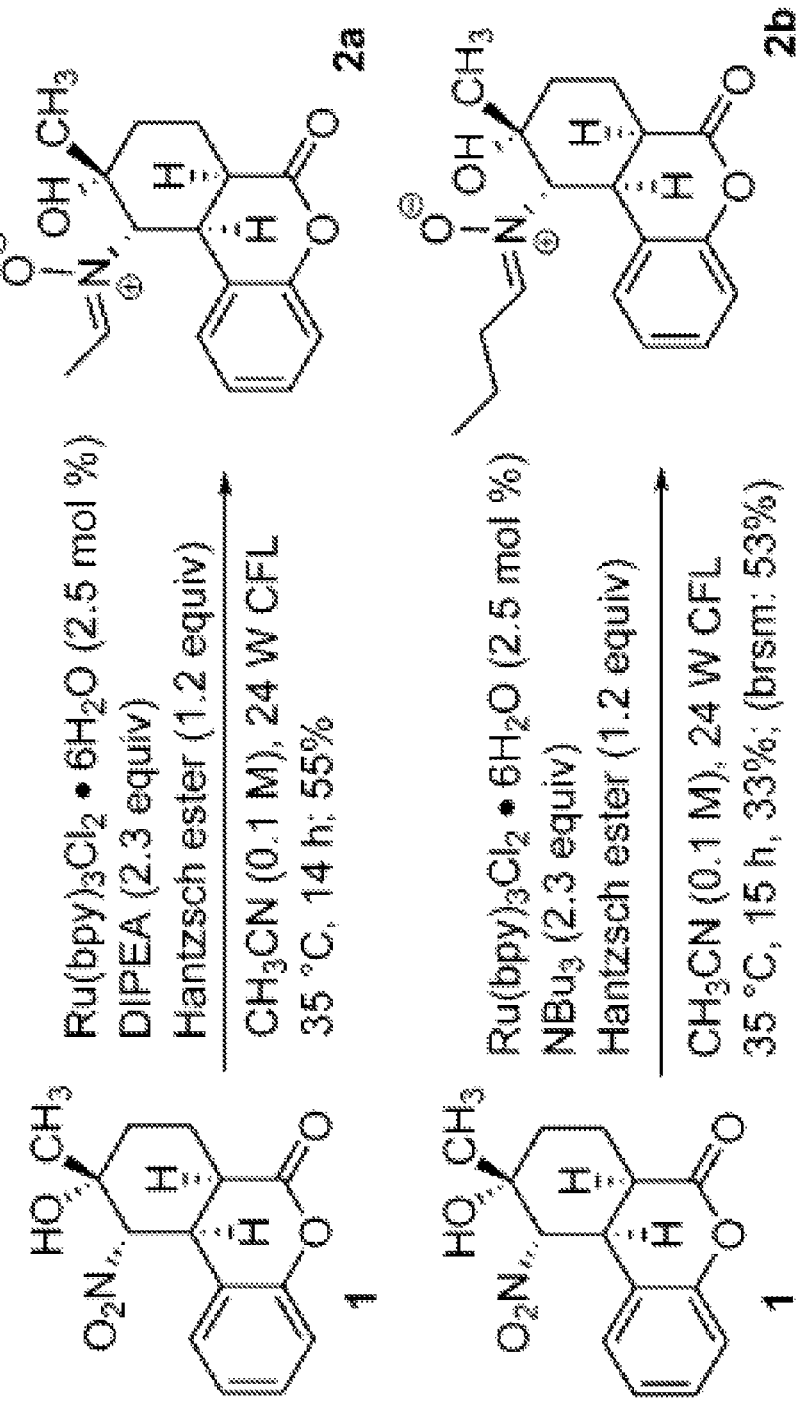
FIG. 2 is a schematic flow diagram showing the preparation of nitrone compounds by second order nitro compound.
Figure 3:
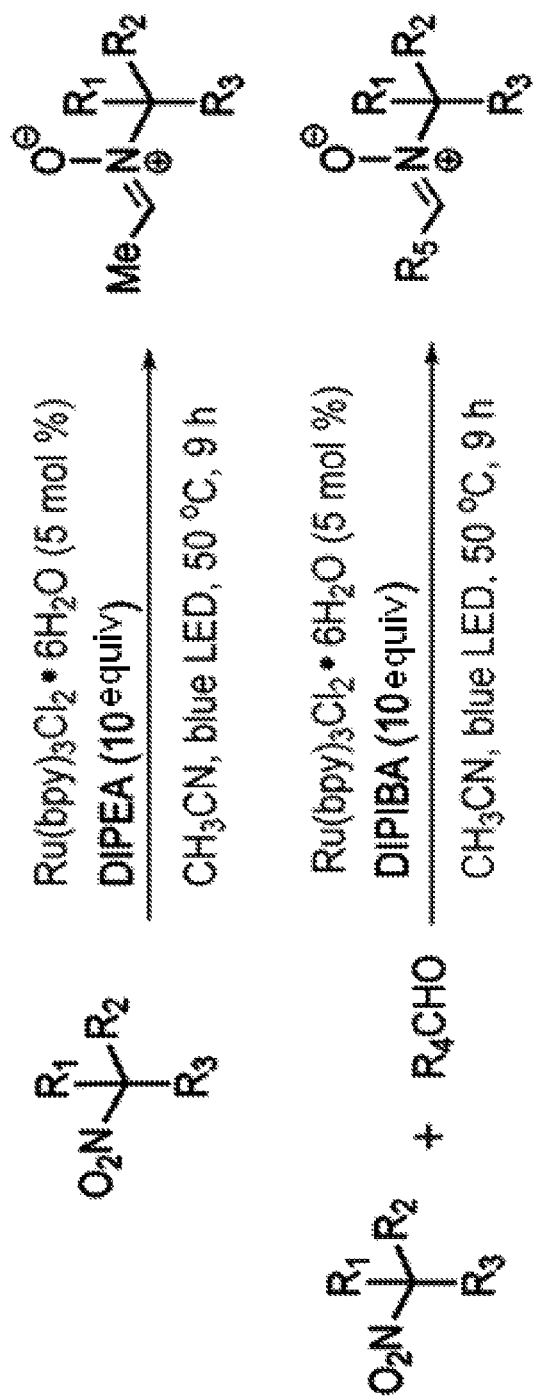
FIG. 3 is a schematic flow diagram showing the preparation of nitrone compounds by third order nitro compound.

Refer to FIGS. 2 and 3, FIG. 2 is a schematic flow diagram showing the preparation of nitrone compounds by second order nitro compound, and FIG. 3 is a schematic flow diagram showing the preparation of nitrone compounds by third order nitro compound. In the method of manufacturing nitrone compound by second order nitro compound, such as the two embodiments as shown in FIG. 2, the nitrone compounds 2a and 2b can be obtained by second order nitro compound represented by compound 1 according to the preceding disclosed method (the detailed parametric conditions are noted in FIG. 2).

And, in the method of manufacturing nitrone compound by third order nitro compound, such as the two embodiments as shown in FIG. 3, the nitrone compounds 4a, 4b, 6a, 6c, 6d, 6e, 6f, 6g, 6h, 6i, 6j and 6k can be obtained by third order nitro compound represented by corresponding compound 3 according to the preceding disclosed method (the detailed parametric conditions are noted in FIG. 3). In another embodiment, with the detailed parametric conditions which are the same as those in FIG. 3, the nitro compound 3 can also be the second order nitro compounds, for example, compounds 3l, 3m or 3n listed in table 1, the nitrone compound 4 can be the nitrone compounds represented by 4a or 4b listed in table 1, and the nitrone compounds 6l, 6m, 6n and 7m can be obtained by the second order nitro compounds 3l, 3m or 3n, respectively, according to the preceding disclosed method.

The nitrone compound represented in table 1 is obtained by reacting 5 mol % catalyst and 0.1 M nitro compound 3. Wherein, in method A, the additive DIPEA is 10 equivalents; in method A', the additive DIPIBA is 10 equivalents; in method B, the additive DIPEA is 10 equivalents and aldehyde compound R$_4$CHO is 5 equivalents; and in method B', the additive DIPIBA is 10 equivalents and aldehyde compound R$_4$CHO is 5 equivalents. The yields of each nitrone compounds are shown in table 1.

TABLE 1

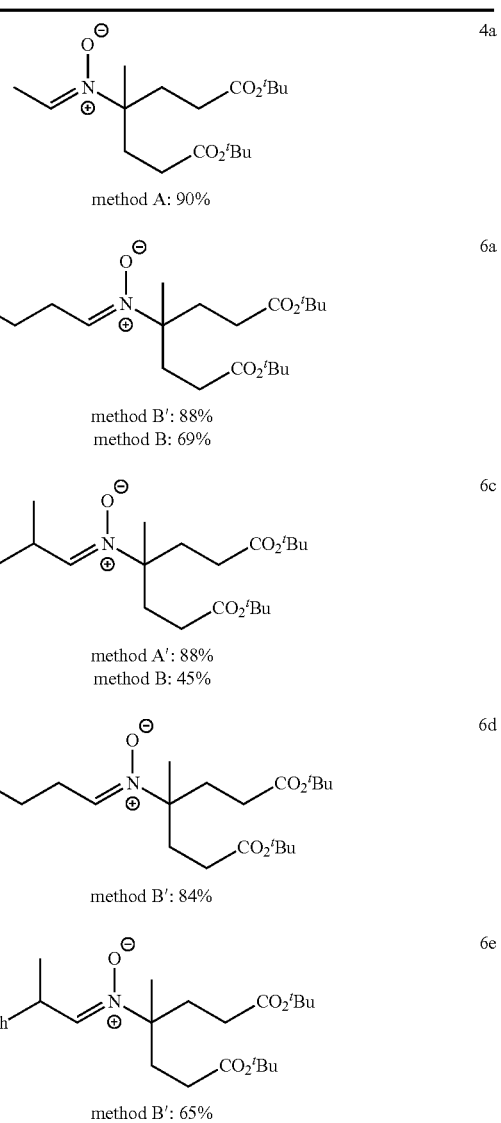

TABLE 1-continued
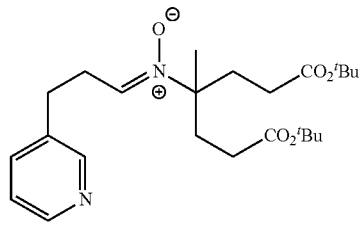
6f
method B': 88%
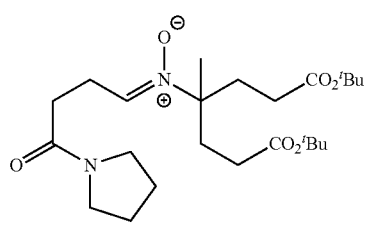
6g
method B': 87%
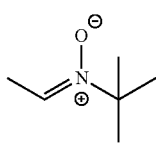
4b
method A: 88%
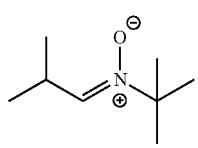
6h
method A': 84%
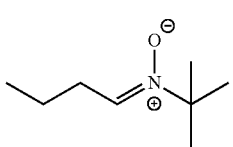
6i
method B': 88%
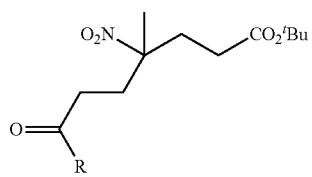
3j R = H
3k R = Me
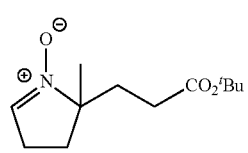
6j
method A': 82%
TABLE 1-continued
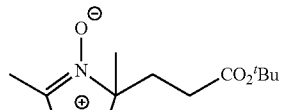
6k
method A': 91%
method A: 90%
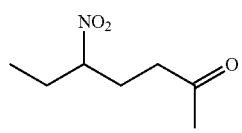
3l
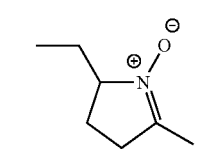
6l
method A': 66%
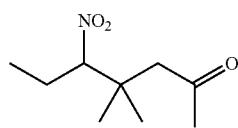
3m
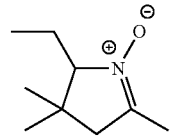
6m
method A': 27%
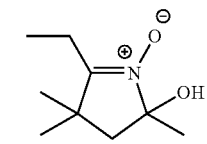
7m
method A': 67%
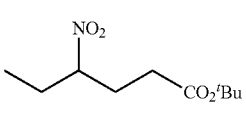
3n
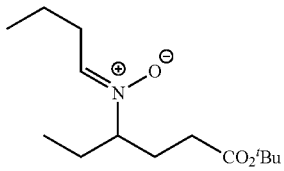
6n
method B': 81%

TABLE 1-continued

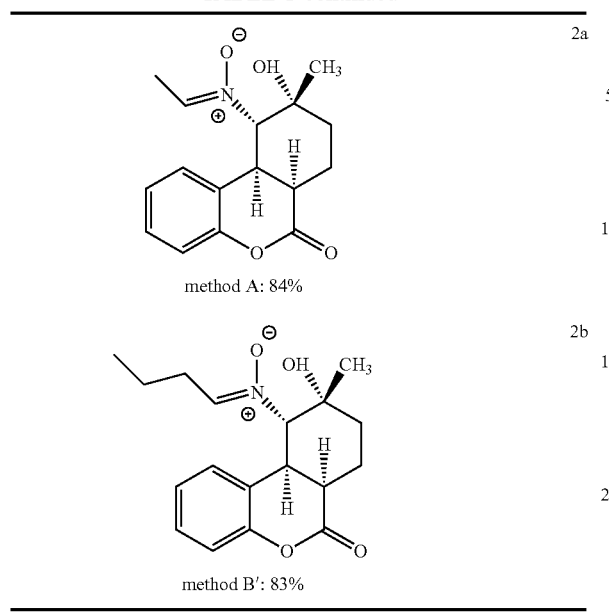

method A: 84% method B': 83%

Figure 4:
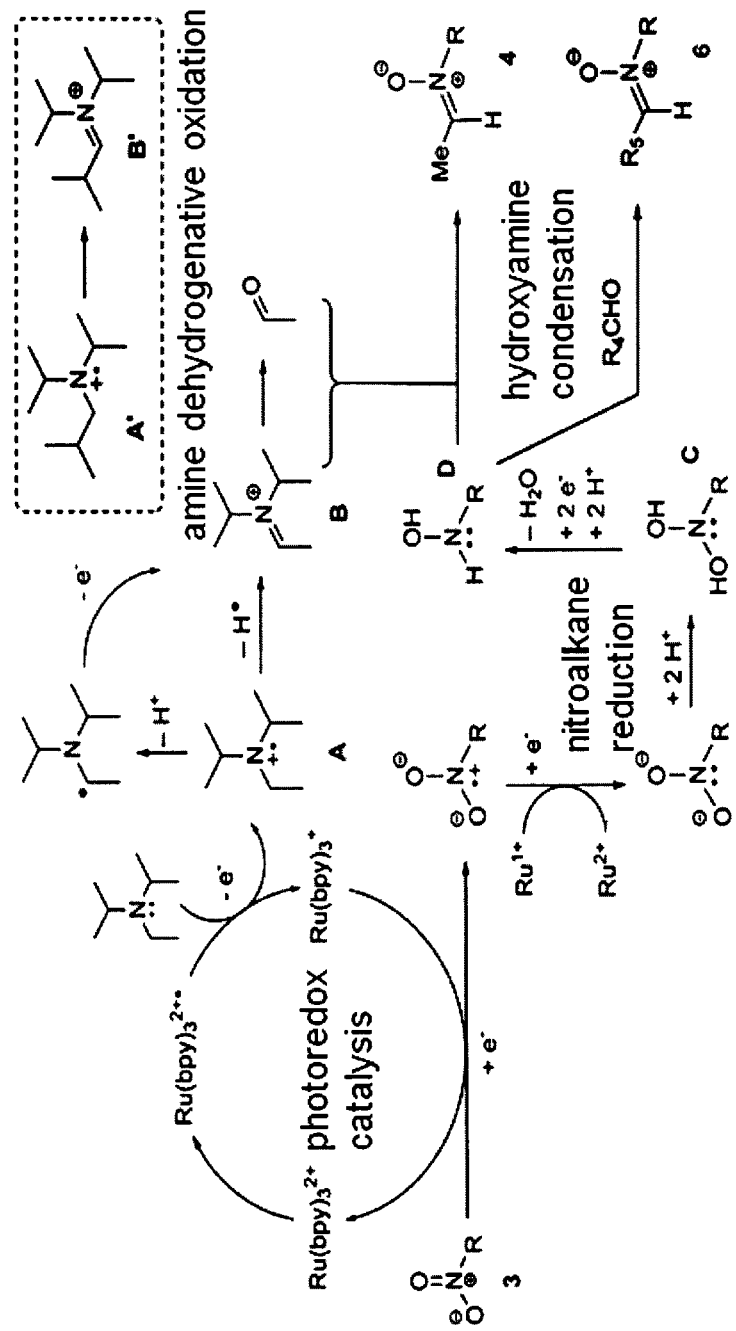
FIG. 4 is a reaction mechanism of the method of manufacturing nitrone compound of the present invention.

Refer to FIG. 4, FIG. 4 is a reaction mechanism of the method of manufacturing nitrone compound of the present invention. As shown in FIG. 4, the photoredox catalyst reaction of the catalyst Ru(bpy$_3$)Cl$_2$·6H$_2$O is performed and then the electron exchange reaction is performed between the Ru(bpy$_3$)Cl$_2$·6H$_2$O and the nitro compound 3 so as to obtain the intermediate of the nitro compound. The intermediate of the nitro compound, the ruthenium ion and hydrogen ion perform a nitoalkane reduction and then react with DIPEA or with DIPIBA and aldehyde compound R$_4$CHO to obtain nitrone compound 4 or 6.

As shown in FIG. 4, when the additive is DIPEA, DIPEA will involve in the reaction (as shown in FIG. 3, Me group of manufactured nitrone compound 4 is from DIPEA). Because steric effect of the additive DIPIBA is bigger than that of DIPEA, DIPIBA is less involved in the reaction (see compound A' and B'). Therefore, the nitrone compounds having various substituents can be manufactured by choosing aldehydes with various functional groups (R$_5$ groups of the nitrone compound 6 and 7 are from R$_4$ of aldehyde compound R$_4$CHO). And, as shown in the following reaction scheme, the nitroalkane reaction of FIG. 4 can be inferred from this reaction scheme, wherein the compound D is corresponding to compound 5a.

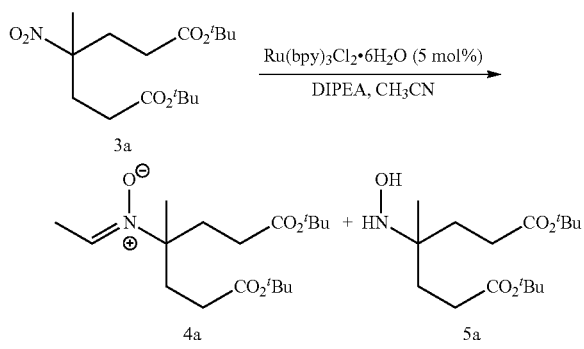

In summary, the photoreaction is performed under visible light by the nitro compound, the catalyst and the additive, and the nitrone compound can be manufactured under mild condition. And, the nitrone compounds having various substituents can be manufactured by choosing various nitro compounds, additives or aldehydes.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A method of manufacturing nitrone compound represented by Formula 1, comprising:
   providing second order or third order nitroalkane represented by Formula 3; and
   performing a photoreaction of the second order or third order nitroalkanes, a catalyst and an additive under visible light to obtain the nitrone compound,
   wherein the catalyst is a compound which produces Ru(bpy)$_3$(II) ion,
   wherein the additive is diisopropylethylamine (DIPEA), diisopropylisobutylamine (DIPIBA) or a derivative of 1,4-Dihydropyridine (DHP),
   wherein a reaction scheme of the photoreaction is shown as below:

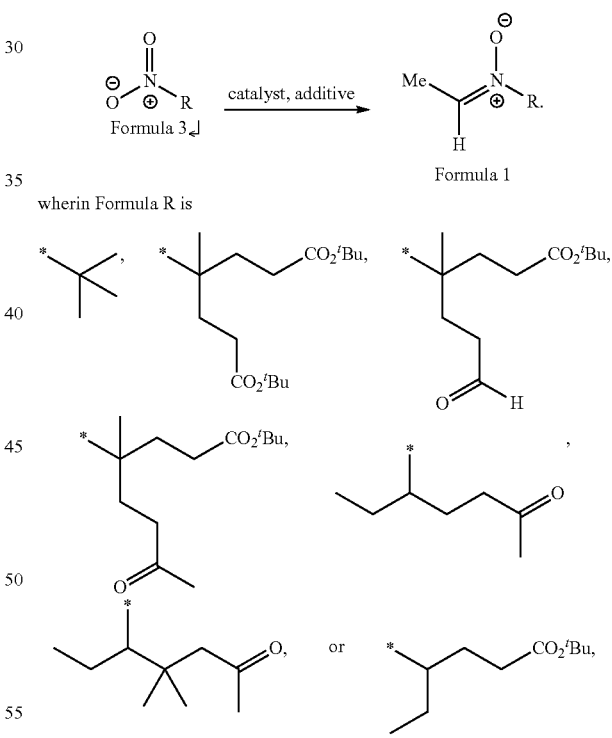

wherin Formula R is and * indicates a binding site.

2. The method of claim 1, wherein the catalyst is Ru(bpy$_3$)Cl$_2$·6H$_2$O, Ru(bpy$_3$)Cl$_2$, Ru(bpy)$_3$(BF$_4$)$_2$, Ru(bpy)$_3$(PF$_6$)$_2$, Ir[dF(CF$_3$)ppy]$_2$(dtbbpy)(PF$_6$) or Ir(ppy)$_2$(dtbbpy)(PF$_6$).

3. The method of claim 1, wherein a wavelength of the visible light is within the range of 350 to 700 nm.

4. The method of claim 3, wherein a wavelength of the visible light is within the range of 450 to 460 nm.

5. The method of claim 1, wherein the derivative of 1,4-Dihydropyridine (DHP) is Hantzsch ester.

6. A method of manufacturing nitrone compound represented by Formula 2, comprising:
   providing second order or third order nitroalkanes represented by Formula 3; and
   performing a photoreaction of the second order or third order nitroalkanes, a catalyst, an additive and an aldehyde compound represented by $R_4CHO$ under visible light to obtain the nitrone compound,
   wherein the catalyst is a compound which produces $Ru(bpy)_3(II)$ ion,
   wherein the additive is diisopropylisobutylamine (DIPIBA),
   wherein a reaction scheme of the photoreaction is shown as below:

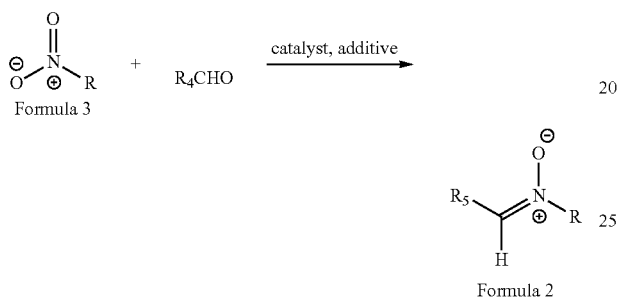

Formula 3

Formula 2 wherein R is

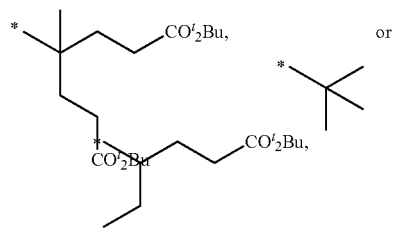

$R_5$ and $R_4$ is

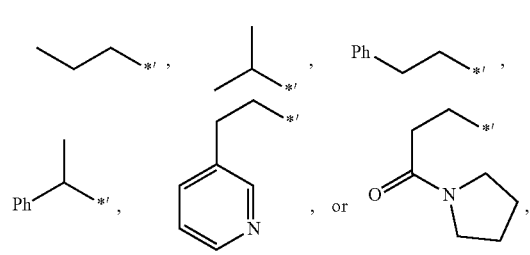

and * and *' indicate binding sites, wherein $R_5$ is the same as $R_4$.

* * * * *